United States Patent [19]
Connors

[11] Patent Number: 4,819,627
[45] Date of Patent: Apr. 11, 1989

[54] CARDIOPULMONARY RESUSCITATION DEVICE

[76] Inventor: Donald J. Connors, 118 S. Midlothian Blvd., Youngstown, Ohio 44507

[21] Appl. No.: 157,841

[22] Filed: Feb. 8, 1988

[51] Int. Cl.$^4$ ............................................. A61M 16/00
[52] U.S. Cl. ............................ 128/203.11; 128/202.28; 128/202.29
[58] Field of Search ...................... 128/202.28, 202.29, 128/203.11, 207.14

[56] References Cited

U.S. PATENT DOCUMENTS

| | | | |
|---|---|---|---|
| 3,013,554 | 12/1961 | Safar et al. | 128/202.28 |
| 3,070,089 | 12/1962 | Dick | 128/205.13 |
| 3,089,485 | 5/1963 | Hirschhorn | 128/202.28 |
| 3,242,921 | 3/1966 | Seeler | 128/203.11 |
| 3,508,543 | 4/1970 | Aulicono | 128/202.28 |
| 3,957,046 | 5/1976 | Harris | 128/203.11 |
| 4,360,017 | 11/1982 | Barlett | 128/207.14 |
| 4,535,765 | 8/1985 | Paoluccio et al. | 128/203.11 |

FOREIGN PATENT DOCUMENTS

| | | | |
|---|---|---|---|
| 0240878 | 9/1960 | Australia | 128/202.28 |
| 0193720 | 1/1965 | Sweden | 128/202.28 |

Primary Examiner—Kyle L. Howell
Assistant Examiner—K. Schaetzle
Attorney, Agent, or Firm—Harpman & Harpman

[57] ABSTRACT

A device having a planar body with communicating flexible tubular members on its opposite sides having a one-way air valve therebetween may be used by a person performing mouth-to-mouth resuscitation on a second person such as in the practice of cardiopulmonary resuscitation commonly referred to as CPR. One of the flexible tubular members is designed to be positioned in the mouth of the person receiving the resuscitation and retained therein by portions of the planar body of the device being held against the person's lips and cheeks while the other of the flexible tubular members is positioned in the mouth of the person performing the mouth-to-mouth resuscitation. The one-way air valve controlling communication between the flexible tubular members is arranged to permit air to be delivered into the mouth of the person receiving the resuscitation and to prevent air from the receiving person's mouth from moving upwardly into the mouth of the person performing the mouth-to-mouth resuscitation. The device prevents saliva, phlegm, or other liquids from entering the mouth of the person performing the mouth-to-mouth resuscitation. The communicating flexible tubular members are designed to be collapsed into a small area to facilitate packaging of the device with the device being formed of a suitable synthetic resin or the like having sufficient resiliency to extend the flexible tubular members into usable positions when the packaging, which primarily maintains the device in sterile condition, is removed.

5 Claims, 2 Drawing Sheets

CARDIOPULMONARY RESUSCITATION DEVICE

BACKGROUND OF THE INVENTION

1. Technical Field

This invention relates to a device used in mouth-to-mouth resuscitation to prevent direct contact between the person performing the resuscitation and the person receiving it so as to protect the person performing the mouth-to-mouth resuscitation from subjection to body fluids and like and disease causing bacteria and/or viruses.

2. Description of the Prior Art

No protective devices are known that are capable of use in mouth-to-mouth resuscitation wherein passage of air from the lungs of one person to the other is performed.

SUMMARY OF THE INVENTION

A device for protecting a person performing mouth-to-mouth resuscitation on another person comprising an elongated thin flat distortable body member having an opening midway between its ends with communicating flexible tubular members on its upper and lower sides in registry with said opening and a one-way flap valve positioned in said opening and movable downwardly into the lower one of said flexible tubular members by air directed thereagainst and engageable in sealing relation against the upper one of said flexible tubular members when air is exhausted from the person receiving the mouth-to-mouth resuscitation as occurs when the person performing the mouth-to-mouth resuscitation removes his mouth from the upper one of the flexible members and releases the devices when the receiving person's sternum (breastbone) is pushed downwardly manually in performing external cardiac compensation to force the blood from the heart through the pulmonary artery to other parts of the body. This action also expels the air from the lungs of the person receiving the mouth-to-mouth resuscitation. The expelled air and any other fluids cannot pass the one-way flap valve and cannot contaminate the upper one of the flexible tubular members.

DESCRIPTION OF THE PREFERRED EMBODIMENT

Figure 2:
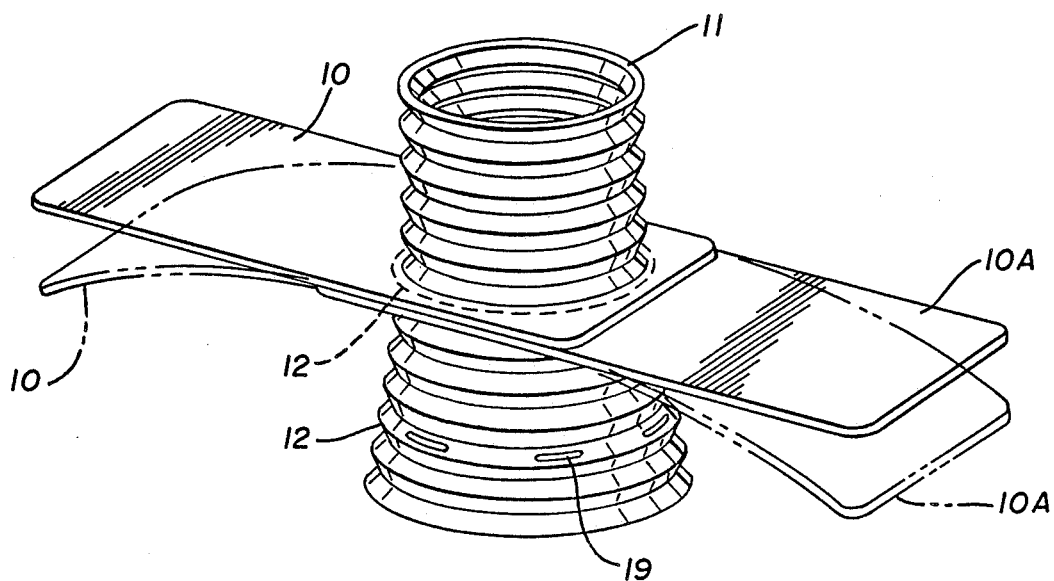
FIG. 2 is a perspective view of the cardiopulmonary resuscitation device in expanded usable shape with broken lines indicating the position of a portion thereof when the device is in use as illustrated in FIG. 1 of the drawings.

In the form of the invention chosen for illustration, the invention is best illustrated in FIG. 2 of the drawings, and by referring thereto it will be seen that it is formed of elongated planar body members 10 and 10A preferably made of resilient resins, such as polyvinyl chloride, and each of which is apertured adjacent one end so that when the apertured ends are overlapped and attached to one another in sealing relation, the apertures are in registry.

Figure 3:
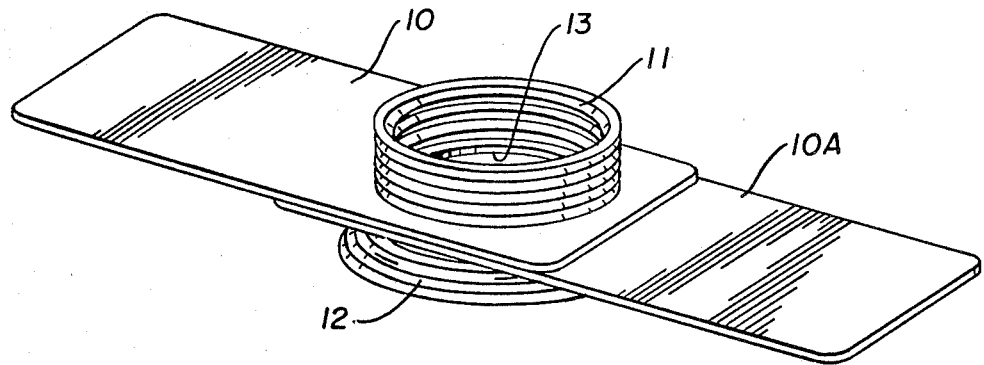
FIG. 3 is a perspective view of the device in collapsed shape as when the same is packaged in a sterile envelope.

Still referring to FIG. 2 of the drawings, it will be seen that an extensible and collapsible flexible tubular member 11 of a known diameter extends upwardly from the upper surface of the elongated planar body member 10 in registry with the aperture therein. The tubular member 11 is preferably integrally formed with the elongated planar body member 10. A second tubular member 12 of a diameter larger than the known diameter of the tubular member 11 extends downwardly from the lower surface of the elongated planar body member 10A and is in registry with the aperture formed therein. The second tubular member 12 is preferably integrally formed with the elongated planar body member 10A and both the tubular body members 11 and 12 are formed with thin walls which are preferably arranged in annular accordian-like configurations so that they can be distorted by moving the same toward each other to form a relatively small dimension as best seen in FIG. 3 of the drawings. The tubular members 11 and 12 are preferably formed of a synthetic resin such as polyvinyl chloride having a memory characteristic that will reshape and reform the tubular members 11 and 12 to full extended shapes as seen in FIGS. 2 and 4 of the drawings when permitted to do so.

Figure 1:
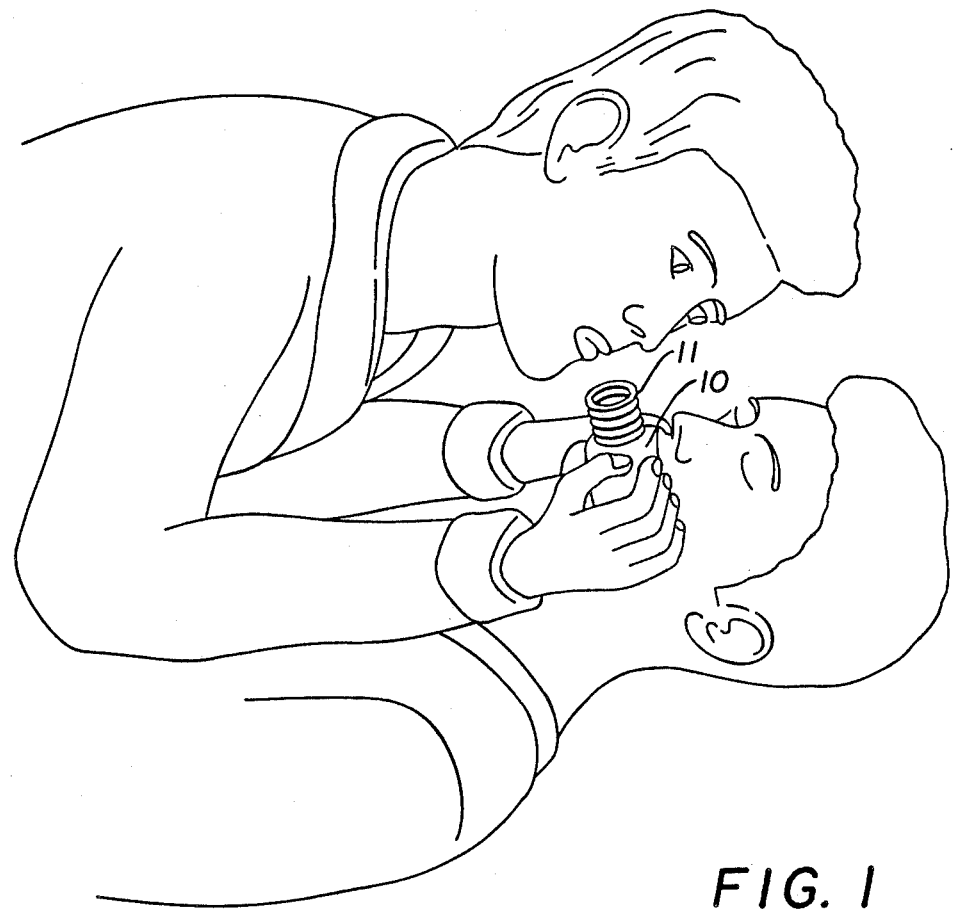
FIG. 1 is a view of a person receiving mouth-to-mouth resuscitation from another person and illustrates the positioning of the device of the invention.

By referring now to FIG. 1 of the drawings, it will be seen that a person to which mouth-to-mouth resuscitation is being given is illustrated as having the device of the invention positioned with the larger tubular member 12 in his mouth and the elongated planar body members 10 and 10A, which are joined to one another and/or integrally formed, are being held downwardly over his lips and cheeks to form a substantially airtight closure. The deformation of the body members 10 and 10A is possible, at least to the extent shown in broken lines in FIG. 2 of the drawings.

Referring again to FIG. 2 of the drawings, it will be seen that the second tubular member 12 tapers outwardly and downwardly with each of its accordian-like configurations being slightly larger than the other in descending relation so that when this tubular member 12 is inserted in a person's mouth as shown in FIG. 1 of the drawings, it tends to be self-retaining therein as it underlies the lips and jaws. At the same time the known diameter of the upper tubular member 11 is of a size conveniently positioned in the mouth of the person administering the mouth-to-mouth resuscitation so that the person administering the mouth-to-mouth resusitation can blow air downwardly through the device.

Figure 4:
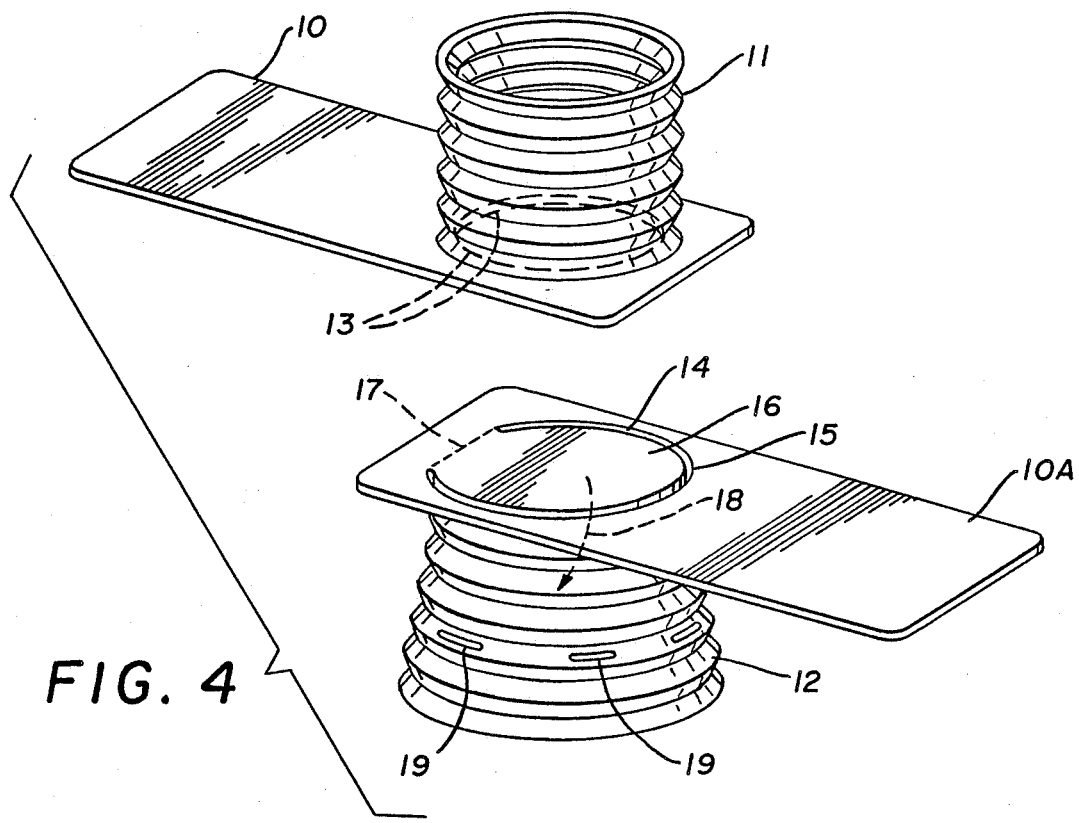
FIG. 4 is an expanded perspective view of the two portions of the device as formed prior to their assembly in sealing relation to one another.

In FIG. 4 of the drawings, the elongated planar body member 10 is illustrated with broken lines showing the aperture 13 therein with the extensible and collapsible flexible tubular member 11 extending upwardly from the elongated planar body member 10 from its point of engagement therewith around the aperture 13. In FIG. 4 of the drawings, the elongated planar body member 10A is illustrated in an as-formed condition wherein an aperture 14 is defined by an approximately 300° circular slit 15 so as to form a one-way flap valve 16 which is hinged to the elongated planar body member 10A by a live hinge 17, which as will be recognized by those skilled in the art as a continuation of the elongated planar body member 10A. A broken line arrow 18 in FIG. 4 of the drawings shows a normal downward deflection of the flap valve 16 when the device is assembled as shown in FIGS. 2 and 3 of the drawings and air is directed downwardly through the device as in a mouth-to-mouth resuscitation.

It will be observed that the substantially circular slit 15 which defines the aperture 14 in the elongated planar body member 10A, is of a larger diameter than the aperture 13 in the elongated planar body member 10 so that the one-way flap valve 16 cannot move upwardly through the aperture 13 but can move freely downwardly in the direction of the broken line arrow 18. The elongated planar body members 10 and 10A are preferably formed in the shapes illustrated in FIG. 4 of the drawings and they are assembled to one another as shown in FIGS. 2 and 3 of the drawings by cementing or heat sealing or otherwise securing the upper surface of the elongated planar body member 10A to the bottom surface of the elongated planar body member 10 so that the device upon being assembled appears as illustrated in FIG. 2 of the drawings and as illustrated in FIG. 3 of the drawings, the extensible and collapsible flexible tubular member 11 and the extensible and collapsible tubular member 12 have been moved into collapsed or retracted position and this shape retained while a sterile protective envelope is positioned in tightly registering all enclosing relation around the device.

It will occur to those skilled in the art that when the device of the invention is used in a mouth-to-mouth resuscitation the air in the lungs of the person receiving the resuscitation must exit the same before further air can be blown thereinto and when the device of the invention is in position in the mouth of the person receiving resuscitation, the one-way flap valve closes the exit path and the person administering the mouth-to-mouth resuscitation must therefore release the device from the lips of the person receiving resuscitation to permit air to exit. The device is provided with several slits 19 in one of the accordian-fold configurations of the second flexible tubular member 12 so that such air exiting the lungs may directly enter the mouth of the person receiving resuscitation and flow therefrom around the elongated planar body member 10 to the atmosphere as it cannot pass the flap valve 16 and enter the first flexible tubular member 11.

While the device as hereinbefore illustrated and described discloses a preferred embodiment, it will occur to those skilled in the art that the device may be formed with the elongated planar body members 10 and 10A in one piece rather than two with the oppositely disposed extensible and collapsible tubular members 11 and 12 integrally formed therewith or formed separately and attached thereto and the one-way valve 16 formed in the single elongated planar body member.

It will be understood that while a suitable material has been referred to as polyvinyl chloride resin, it may be desirable to form the entire device of latex using an appropriately shaped molding body and dipping, forming and setting the latex body of the device thereon and subsequently cutting the aperture 14 so as to form the flap valve 16 in such a modified device.

Although but one embodiment of the present invention has been illustrated and described, it will be apparent to those skilled in the art that various changes and modifications may be made therein without departing from the spirit of the invention and having thus disclosed my invention, what I claim is:

1. A device for use in mouth-to-mouth resuscitation and cardiopulmonary resuscitation comprising a planar body member, said planar body member comprising a first planar body member and a second planar body member, each having upper and lower surfaces and each having an aperture therein adjacent one end thereof, said first and second planar body members secured to one another in superimposed relation with said apertures in registry with one another, a first tubular member positioned on the upper surface of said first planar body member in communication with said aperture therein and a second tubular member positioned on the lower surface of said second planar body member in communication with said aperture therein, a one-way flap valve member formed integrally with said second planar body member so as to be largely separated therefrom and connected thereto by a live hinge portion and positioned for movement toward and away from said aperture in said second planar body member so as to permit fluid entering the device through the first tubular member and prevent fluid entering the device through said second tubular member from entering said first tubular member.

2. The device for use in mouth-in-mouth resuscitation and cardiopulmonary resuscitation set forth in claim 1 wherein said planar body member is flexible and distortable and is of a length greater than its width and said apertures are midway between its ends.

3. The device for use in mouth-to-mouth resuscitation and cardiopulmonary resuscitation set forth in claim 1 and wherein said first and second tubular members are formed with accordian-like configurations so as to be extensible and collapsible.

4. The device for use in mouth-to-mouth resuscitation and cardiopulmonary resuscitation set forth in claim 1 and wherein at least one slit is formed in said second tubular member arranged to permit fluid to flow therethrough.

5. The device for use in mouth-to-mouth resuscitation and cardiopulmonary resuscitation set forth in claim 1 and wherein said second tubular member tapers downwardly and outwardly from the lower surface of said planar body member so as to form a progressively widening configuration for retention in the mouth of a person receiving said device.

* * * * *